(12) United States Patent
Sebag et al.

(10) Patent No.: US 6,589,539 B1
(45) Date of Patent: Jul. 8, 2003

(54) COSMETIC AND DERMATOLOGICAL COMPOSITIONS COMPRISING CROSSLINKED AND BRANCHED AMPHOTERIC COPOLYMERS AND THEIR USE

(75) Inventors: Henri Sebag, Paris (FR); Claude Dubief, Le Chesnay (FR); Serge Restle, Saint-Prix (FR)

(73) Assignee: L'Oreal S.A., Paris (FR)

( * ) Notice: Subject to any disclaimer, the term of this patent is extended or adjusted under 35 U.S.C. 154(b) by 204 days.

(21) Appl. No.: 09/617,129

(22) Filed: Jul. 14, 2000

(30) Foreign Application Priority Data

Jul. 16, 1999 (FR) .............................. 99 09266

(51) Int. Cl.⁷ ................................. A61K 7/00
(52) U.S. Cl. ....................................... 424/401
(58) Field of Search .................... 424/401, 63, 64, 424/70.1, 70.11, 70.16, 61, 59, DIG. 1, DIG. 2, DIG. 4; 510/119, 130, 136

(56) References Cited

U.S. PATENT DOCUMENTS 4,814,101 A    3/1989  Schieferstein et al.
4,898,725 A  * 2/1990  Hoeffkes et al. .............. 424/70
6,361,768 B1 * 3/2002  Galleguillos et al. ....... 424/401

FOREIGN PATENT DOCUMENTS

| EP | 0 269 243 | 6/1988 |
| EP | 0 283 817 | 9/1988 |
| WO | WO 94/18935 | 9/1994 |
| WO | WO 97/35544 | 10/1997 |
| WO | WO 98/44012 A1 * | 10/1998 |
| WO | WO 00/39176 A1 * | 7/2000 |

* cited by examiner

Primary Examiner—Jose' G. Dees
Assistant Examiner—Marina Lamm
(74) Attorney, Agent, or Firm—Finnegan, Henderson, Farabow, Garrett & Dunner, L.L.P.

(57) ABSTRACT

The use in and for the preparation of both cosmetic and/or dermatological compositions comprising at least one amphoteric copolymer that is crosslinked and/or branched and derived, e.g., from a mixture comprising at least one monomer selected from acrylate, methacrylate, acrylamide, and methacrylamide monomers comprising at least one $C_8$–$C_{30}$ fatty chain. Another subject of the invention is the application of the composition for the treatment of keratinous materials and in particular of the skin, hair, eyelashes, and nails.

47 Claims, No Drawings

COSMETIC AND DERMATOLOGICAL COMPOSITIONS COMPRISING CROSSLINKED AND BRANCHED AMPHOTERIC COPOLYMERS AND THEIR USE

The present invention relates to compositions comprising at least one amphoteric copolymer that is crosslinked and/or branched and derived e.g., from a mixture comprising at least one monomer selected from acrylate, methacrylate, acrylamide, and methacrylamide monomers comprising at least one $C_8$–$C_{30}$ fatty chain, and to the preparation of cosmetic and/or dermatological compositions comprising these compositions.

The use of conditioning polymers, in particular cationic and amphoteric polymers, to facilitate the disentanglement of the hair or to impart softness and suppleness to it has already been recommended in cosmetic compositions for the skin and for both the washing and care of the hair. However, the use of cationic polymers for this purpose has various disadvantages. Because of their high affinity for the hair, some of these cationic polymers become substantially deposited during repeated use, which leads to undesirable effects such as an unpleasant feel, stiffening of the hair, and interfiber adhesion, which affect hairstyling. These disadvantages are accentuated in the case of fine hair, which lacks hold, vitality, and body.

The use of amphoteric polymers such as those described in patent application EP-A-269,243, the disclosure of which is incorporated herein by reference, has also been recommended for improving the conditioning properties of hair products. However, compositions containing only these polymers do not make it possible to obtain adequate softness and disentanglement.

One of the objectives of the present invention is therefore to use, in cosmetic and dermatological compositions, polymers that provide good cosmetic properties such as disentanglement and a soft feel.

The applicant has surprisingly discovered that these objectives could be achieved by using particular crosslinked and branched copolymers in and for the preparation of cosmetic and dermatological compositions.

It has been discovered, in particular, that the compositions obtained according to the invention can provide in certain embodiments an improvement in disentanglement (in particular on moistened hair) as well as an improvement in the softness of the hair. In addition, in certain embodiments, the hair is not made heavy by repeated applications.

Moreover, the compositions of the invention, when applied to the skin, can provide improvement in the softness of the skin.

A subject of the invention is the use, as cosmetic products, of crosslinked and/or branched amphoteric polymers, which will be defined in greater detail in the remainder of the description.

Indeed, the particular crosslinked and branched copolymers of the invention can in particular be used in and for the preparation of hair products for conditioning the hair. They can also be used in and for the preparation of moisturizing care or make-up products for the skin or the lips, which may contain active agents without leading to a sticky deposition.

A subject of the present invention is the use in and for the preparation of cosmetic and/or dermatological compositions comprising at least one amphoteric copolymer that is crosslinked and/or branched and capable of being obtained by the copolymerization of a mixture that comprises:

1) at least one monomer selected from the monomers of formula (Ia) and (Ib):

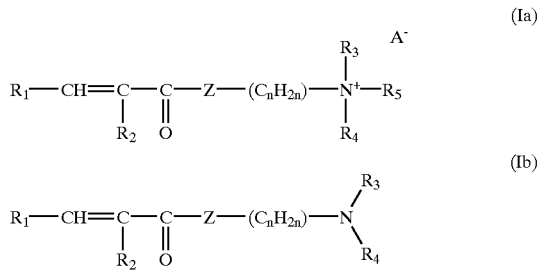

wherein $R_1$ and $R_2$, which are identical or different, are each selected from a hydrogen atom and a methyl radical; $R_3$, $R_4$, and $R_5$, which are identical or different, are each selected from linear and branched alkyl radicals having from 1 to 30 carbon atoms; Z is selected from an NH group and an oxygen atom; n is an integer ranging from 2 to 5; and $A^-$ is an anion selected from anions derived from organic and inorganic acids, such as a methosulphate anion or a halide, such as chloride or bromide;

2) at least one monomer of formula (II):

wherein $R_6$ and $R_7$, which are identical or different, are each selected from a hydrogen atom and a methyl radical; and $Z_1$ is selected from an OH group and a $NHC(CH_3)_2CH_2SO_3H$ group;

3) at least one monomer of formula (III):

wherein $R_6$ and $R_7$, which are identical or different, are each selected from a hydrogen atom and a methyl radical; X is selected from an oxygen atom and a nitrogen atom; and $R_8$ is selected from linear and branched alkyl radicals having from 1 to 30 carbon atoms; and 4) at least one agent selected from crosslinking and branching agents; wherein at least one of the monomers of formulae (Ia), (Ib), and (III) comprises at least one fatty chain having from 8 to 30 carbon atoms; and wherein said monomers of formulae (Ia), (Ib), (II), and (III) may be optionally quaternized, for example with a $C_1$–$C_4$ alkyl halide or a $C_1$–$C_4$ dialkyl sulphate.

Representative monomers of formulae (Ia) and (Ib) of the present invention are selected from dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, and dimethylaminopropylacrylamide.

In another embodiment, the monomers of formula (Ia) are selected from acrylamidopropyltrimethylammonium chloride and methacrylamidopropyltrimethylammonium chloride. In yet another embodiment, the monomer of formula (Ia) is acrylamidopropyltrimethylammonium chloride.

Representative monomers of formula (II) of the present invention are selected from acrylic acid, methacrylic acid, crotonic acid, 2-methylcrotonic acid, 2-acrylamido-2-methyl propanesulphonic acid, and 2-methacrylamido-2-methylpropanesulphonic acid. In yet another embodiment, the monomer of formula (II) is acrylic acid.

Representative monomers of formula (III) of the present invention are selected from $C_{12}$–$C_{22}$ alkyl acrylates and $C_{12}$–$C_{22}$ alkyl methacrylates, and in another embodiment from $C_{16}$–$C_{18}$ alkyl acrylates and $C_{16}$–$C_{18}$ alkyl methacrylates.

Representative crosslinking and branching agents are selected from N,N'-methylenebisacrylamide, triallylmethylammonium chloride, allyl methacrylate, n-methylolacrylamide, polyethylene glycol dimethacrylates, ethylene glycol dimethacrylate, diethylene glycol dimethacrylate, 1,6-hexanediol dimethacrylate, and allyl sucrose.

The compounds constituting the amphoteric polymers of the invention can be neutralized and/or quaternized.

The present invention also relates to cosmetic and/or dermatological compositions comprising, in a cosmetically acceptable medium, at least one amphoteric copolymer that is crosslinked and/or branched and capable of being obtained by the copolymerization of a mixture of compounds described above.

Other objects will be apparent to one of ordinary skill in the art in light of the description and of the examples which follow.

The copolymers of the invention are can be crosslinked, branched or both crosslinked and branched copolymers, which are either soluble or dispersible in water, lower ($C_1$–$C_4$) alcohol(s), or mixtures of water and lower alcohol(s).

The crosslinked and branched copolymers in accordance with the present invention have a weight-average molecular mass generally greater than 1000. In certain embodiments, the weight-average molecular mass ranges from 10,000 to 10,000,000, and in yet other embodiments, from 100,000 to 8,000,000.

The reduced viscosity may be used as a means of determining the weight-average molecular weight according to the present invention. The values indicated here are determined from a Ubbelohde capillary viscometer with a polymer concentration of 0.05% in a 1M NaCl solution at pH7 and at 30° C.

It is also possible to use gel permeation chromatography as an alternative method.

In certain embodiments, the copolymers of the invention are derived from a mixture comprising from 1 mol % to 99 mol %, also from 20 mol % to 95 mol %, and also further from 25 mol % to 75 mol % of monomer(s) of formulae (Ia) and (Ib).

The mixture may also comprise from 1 mol % to 80 mol %, also from 5 mol % to 80 mol %, and further also from 25 mol % to 75 mol % of monomer(s) of formula (II).

The content of monomer(s) of formula (III) is generally ranging from 0.1 mol % to 70 mol %, also from 1 mol % to 50 mol %, and further also from 1 mol % to 10 mol %.

The content of crosslinking and branching agents generally ranges from 0.0001 mol % to 1 mol % and also from 0.0001 mol % to 0.1 mol %.

The molar ratio between the monomer(s) of formulae (Ia) and (Ib) and the monomer(s) of formula (II) generally varies from 20:80 to 95:5 and also from 25:75 to 75:25.

The copolymers of the invention may be prepared by conventional polymerization techniques in solution. For example, a process may comprise:

loading the compounds into a reactor provided with an agitator;

adjusting the total monomer concentration on the order of 10% to 25%;

adjusting the pH of the mixture to a value varying from 3 to 6.5;

purging with nitrogen;

initiating the polymerization with sodium persulphate; and diluting with water in the presence of sodium bisulphite after reaching the exothermic peak, this being in order to reach a polymer concentration on the order of 4% to 8%.

The cosmetic and dermatological compositions according to the invention therefore comprise, in a cosmetically acceptable carrier, amphoteric polymers as described below, for applications as varied as those encountered, for example, in the hair, make-up, and skin care fields, or any other cosmetic field in which the use of a film-forming substance is desirable or sought.

The crosslinked and branched copolymers according to the invention may be used alone as conditioning polymers or alternatively as an additive for conventional conditioning agents in and for the preparation of cosmetic and dermatological compositions.

The copolymer concentration in the cosmetic and dermatological compositions of the invention generally ranges from 0.01% to 50%, and also from 0.1% to 20% of the total weight of the composition. It varies according to the application envisaged, cosmetic and/or dermatological.

The compositions according to the invention may be provided in any form appropriate for topical application, such as in the form of solutions of the lotion or serum type; in the form of gels; in the form of emulsions obtained by dispersion of a fatty phase in an aqueous phase (O/W) or by dispersion of an aqueous phase in a fatty phase (W/O), having a liquid consistency thickened to a greater or lesser degree such as milks and creams, which are unctuous to a greater or lesser degree; and in the form of dispersions. These compositions are prepared according to the customary methods.

The compositions according to the invention may be used as hair styling products, such as for the washing, care, conditioning, retention of the hair style, shaping, dyeing, bleaching, permanent waving, or straightening of the hair.

The leave-in hair compositions according to the invention can be hairstyling products such as hair-setting lotions, blow-drying lotions, and fixing and styling compositions such as lacquers and sprays. The lotions may be packaged in various forms, such as in vaporizers, pump dispensers, and aerosol containers in order to ensure application of the composition in vaporized form or in foam form. Such forms of packaging are recommended, for example, when it is desirable to obtain a spray or a foam for fixing or treating the hair.

The rinse-off hair compositions can also be hairstyling shampoos and/or conditioners or alternatively rinse-off hair conditioners.

The compositions of the invention may also be used as care and/or hygiene products such as creams for the protection, treatment, or care of the face, the hands, or the body; protective or care body milks; and lotions, gels, or foams for the care of the skin and of the mucous membranes and for cleansing the skin.

The compositions of the invention can also be used as make-up removers. The compositions may be make-up products, such as nail varnishes and care bases for the nails.

The cosmetically acceptable carrier of the compositions according to the invention preferably comprises water, one or more cosmetically acceptable organic solvents, or alternatively a mixture of water and one or more cosmetically acceptable organic solvents.

Among these organic solvents, lower $C_1$–$C_4$ alcohols such as ethanol are more particularly used.

The crosslinked and branched copolymers according to the invention are either dissolved or dispersed in the carrier of the compositions of the invention.

The compositions may, in addition, of course further comprise various adjuvants intended to make them acceptable in a particular cosmetic application.

The compositions according to the invention may further comprise at least one conventional cosmetic additive selected from fatty substances such as mineral and animal oils; animal, fossil, mineral, and synthetic waxes; organic solvents; thickening agents; softeners; antifoaming agents; moisturizing agents; humectants; treatment agents (agents for stopping hair loss and the like); antiperspirants; alkalinizing agents; UV-A, UV-B, and broad-band sunscreening agents; colorants; pigments; oxidizing agents; reducing agents; perfumes; plasticizers; preservatives; anionic, cationic, nonionic, and amphoteric organic polymers; and propellants (when the compositions are provided in aerosol form).

Advantageously, the polymers of the invention may be combined with at least one compound selected from water-insoluble carboxylic acid esters, antidandruff agents, silicones in particular water-insoluble silicones, fixing and conditioning polymers, and conditioning agents selected from synthetic oils, vegetable oils, vegetable waxes, and ceramide-type compounds.

Of course, persons skilled in the art will be careful to choose the abovementioned optional additional compound(s) such that the advantageous properties intrinsically attached to the compositions according to the invention are not, or not substantially, impaired by the addition(s) envisaged.

A subject of the invention is also a method of cosmetic treatment of keratinous materials such as the skin, hair, scalp, eyelashes, eyebrows, nails, and lips, characterized in that it comprises applying thereto a composition as defined above.

FORMULATION EXAMPLES

Example 1

|  | A Comparative | B According to the invention |
|---|---|---|
| Lauryl ether sulphate containing 2.2 mol of ethylene oxide | 8% AS | 8% AS |
| Sodium N-cocoylamidoethyl-N-ethoxycarboxymethylglycinate | 4% AS | 4% AS |
| Polymer 1: MAPTAC(49)/AA(49)/SMA(2) | 1% AS | — |
| Polymer 2: MAPTAC(49)/AA(49)/SMA(1.9994)/MBA(0.0006) | — | 1% AS |
| Water qs | 100 | 100 |

MAPTAC = methacrylamidopropyltrimethylammonium chloride
M = acrylic acid
SMA = stearyl methacrylate
MBA = N,N'-methylenebisacrylamide Compositions A and B are applied in an amount of from 1 g to 2.7 g to natural hair locks. After an exposure time of 5 minutes, the hair is rinsed and dried.

A comparative test relating to the evaluation of the smooth/silky nature of the locks was carried out on both wet and dry locks with a panel of 10 testers.

On a scale on which the differences in the state of smoothness/silkiness are evaluated from 1 (only very slightly marked difference) to 4 (very marked difference), a sum of the differences of +22 in favour of composition B according to the invention is observed for all the testers.

This composition therefore leads to a significantly greater smoothness/silkiness of the hair than that obtained with comparison composition A.

Example 2

| Lauryl ether sulphate containing 2.2 mol of ethylene oxide | 8% AS |
|---|---|
| Sodium N-cocoylamidoethyl-N-ethoxycarboxymethylglycinate | 4% AS |
| Silicone PDMS (500,000) | 1.5% |
| Polymer MAPTAC(49)/AA(49)/SMA(1.9994)/MBA(0.0006) | 1% AS |
| Water qs | 100 |

This composition, when applied to the hair, leads to remarkable cosmetic hair fibre conditioning properties after rinsing.

What is claimed is:

1. A process of preparing cosmetic and/or dermatological compositions, which comprise at least one amphoteric copolymer that is crosslinked and/or branched, wherein said process comprises the copolymerization of a mixture, which comprises:

1) at least one monomer selected from the monomers of formulae (Ia) and (Ib):

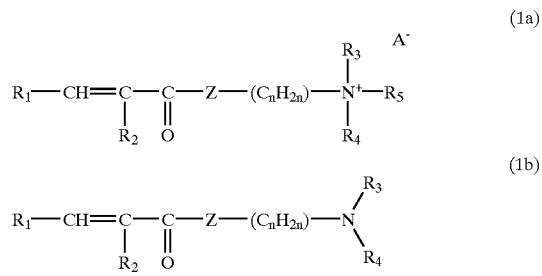

wherein $R_1$ and $R_2$, which are identical or different, are each selected from a hydrogen atom and a methyl radical; $R_3$, $R_4$, and $R_5$, which are identical or different, are each selected from linear and branched alkyl radicals having from 1 to 30 carbon atoms; Z is selected from an NH group and an oxygen atom; n is an integer ranging from 2 to 5; and $A^-$ is an anion selected from anions derived from organic and inorganic acids;

2) from 25 mol % to 75 mol % of at least one monomer of formula (II):

wherein $R_6$ and $R_7$, which are identical or different, are each selected from a hydrogen atom and a methyl radical; and $Z_1$ is selected from an OH group and a $NHC(CH_3)_2CH_2SO_3H$ group;

3) at least one monomer of formula (III):

$$R_6-\underset{H}{C}=CR_7-CO-XR_8 \quad (III)$$

wherein $R_6$ and $R_7$, which are identical or different, are each selected from a hydrogen atom and a methyl radical; X is selected from an oxygen atom and a nitrogen atom; and $R_8$ is selected from linear and branched alkyl radicals having from 1 to 30 carbon atoms; and
   4) at least one agent selected from crosslinking and branching agents; wherein at least one of the monomers of formulae (Ia), (Ib), and (III) comprises at least one fatty chain having from 8 to 30 carbon atoms; and wherein said monomers of formulae (Ia), (Ib), (I), and (III) may be quaternized.

2. The process according to claim 1, wherein the at least one monomer selected from the monomers of formulae (Ia) and (Ib) is selected from dimethylaminoethyl methacrylate, dimethylaminoethyl acrylate; diethylaminoethyl methacrylate, diethylaminoethyl acrylate, dimethylaminopropyl methacrylate, dimethylaminopropyl acrylate, dimethylaminopropylmethacrylamide, and dimethylaminopropylacrylamide.

3. The process according to claim 1, wherein the monomers of formula (Ia) are selected from acrylamidopropyltrimethylammonium chloride and methacrylamidopropyltrimethylammonium chloride.

4. The process according to claim 1, wherein the at least one monomer of formula (II) is selected from acrylic acid, methacrylic acid, crotonic acid, 2-methylcrotonic acid, 2-acrylamido-2-methylpropanesulphonic acid, and 2-methacrylamido-2-methyl propanesulphonic acid.

5. The process according to claim 1, wherein the at least one monomer of formula (III) is selected from $C_{12}$–$C_{22}$ alkyl acrylates and $C_{12}$–$C_{22}$ alkyl methacrylates.

6. The process according to claim 1, wherein the at least one monomer of formula (III) is selected from $C_{16}$–$C_{18}$ alkyl acrylates and $C_{16}$–$C_{18}$ alkyl methacrylates.

7. The process according to claim 1, wherein the at least one agent is selected from N,N'-methylenebisacrylamide, triallylmethylammonium chloride, allyl methacrylate, n-methylolacrylamide, polyethylene glycol dimethacrylates, ethylene glycol dimethacrylate, diethylene glycol dimethacrylate, 1,6-hexanediol dimethacrylate, and allyl sucrose.

8. The process according to claim 1, wherein the at least one monomer selected from the monomers of formulae (Ia) and (Ib) is present in the mixture in amounts ranging from 1 mol % to 99 mol %.

9. The process according to claim 1, wherein the at least one monomer selected from the monomers of formulae (Ia) and (Ib) is present in the mixture in amounts ranging from 20 mol % to 95 mol %.

10. The process according to claim 1, wherein the at least one monomer selected from the monomers of formulae (Ia) and (Ib) is present in the mixture in amounts ranging from 25 mol % to 75 mol % of the copolymer.

11. The process according to claim 1, wherein the at least one monomer of formula (III) is present in the mixture in amounts ranging from 0.1 mol % to 70 mol %.

12. The process according to claim 1, wherein the at least one monomer of formula (III) is present in the mixture in amounts ranging from 1 mol % to 50 mol %.

13. The process according to claim 1, wherein the at least one monomer of formula (III) is present in the mixture in amounts ranging from 1 mol % to 10 mol %.

14. The process according to claim 1, wherein the at least one agent is present in the mixture in amounts ranging from 0.0001 mol % to 1 mol %.

15. The process according to claim 1, wherein the at least one agent is present in the mixture in amounts ranging from 0.0001 mol % to 0.1 mol %.

16. The process according to claim 1, wherein the molar ratio between the at least one monomer selected from the monomers of formulae (Ia) and (Ib) and the at least one monomer of formula (II) varies from 20:80 to 95:5.

17. The process according to claim 1, wherein the molar ratio between the at least one monomer selected from the monomers of formulae (Ia) and (Ib) and the at least one monomer of formula (II) varies from 25:75 to 75:25.

18. The process according to claim 1, wherein the at least one amphoteric copolymer has a weight-average molecular weight, determined by viscometry, greater than 1000.

19. The process according to claim 1, wherein the at least one amphoteric copolymer has a weight-average molecular weight, determined by viscometry, ranging from 10,000 to 10,000,000.

20. The process according to claim 1, wherein the at least one amphoteric copolymer has a weight-average molecular weight, determined by viscometry, ranging from 100,000 to 8,000,000.

21. A cosmetic and/or dermatological composition comprising in a cosmetically acceptable carrier, at least one amphoteric copolymer that is crosslinked and/or branched, copolymerized from a mixture, which comprises:
   1) at least one monomer selected from the monomers of formulae (Ia) and (Ib):

$$R_1-CH=\underset{R_2}{C}-\underset{O}{\overset{\|}{C}}-Z-(C_nH_{2n})-\overset{R_3}{\underset{R_4}{N^+}}-R_5 \quad A^- \quad (Ia)$$

$$R_1-CH=\underset{R_2}{C}-\underset{O}{\overset{\|}{C}}-Z-(C_nH_{2n})-N\overset{R_3}{\underset{R_4}{\diagdown}} \quad (Ib)$$

wherein $R_1$ and $R_2$, which are identical or different, are each selected from a hydrogen atom and a methyl radical; $R_3$, $R_4$, and $R_5$, which are identical or different, are each selected from linear and branched alkyl radicals having from 1 to 30 carbon atoms; Z is selected from an NH group and an oxygen atom; n is an integer ranging from 2 to 5; and $A^-$ is an anion selected from anions derived from organic and inorganic acids;

2) from 25 mol % to 75 mol % of at least one monomer of formula (II):

$$R_6-\underset{H}{C}=CR_7-CO-Z_1 \quad (II)$$

wherein $R_6$ and $R_7$, which are identical or different, are each selected from a hydrogen atom and a methyl radical; and $Z_1$ is selected from an OH group and a $NHC(CH_3)_2CH_2SO_3H$ group;

3) at least one monomer of formula (III):

wherein $R_6$ and $R_7$, which are identical or different, are each selected from a hydrogen atom and a methyl radical; X is selected from an oxygen atom and a nitrogen atom; and $R_8$ is selected from linear and branched alkyl radicals having from 1 to 30 carbon atoms; and 4) at least one agent selected from crosslinking and branching agents; wherein at least one of the monomers of formulae (Ia), (Ib), and (III) comprises at least one fatty chain having from 8 to 30 carbon atoms; and wherein said monomers of formulae (Ia), (Ib), (II), and (III) may be quaternized.

22. The composition according to claim 21, wherein said anion is selected from methosulphate anions, chloride, and bromide.

23. The composition according to claim 21, wherein the at least one amphoteric copolymer concentration in the cosmetic and/or dermatological composition ranges from 0.01% to 50% by weight relative to the total weight of the composition.

24. The composition according to claim 21, wherein the at least one amphoteric copolymer concentration in the cosmetic and/or dermatological composition ranges from 0.1% to 20% by weight relative to the total weight of the composition.

25. The composition according to claim 21, wherein the cosmetically acceptable carrier comprises at least one carrier selected from water and cosmetically acceptable organic solvents.

26. The composition according to claim 25, wherein the cosmetically acceptable organic solvents are selected from lower $C_1$–$C_4$ alcohols.

27. The composition according to claim 21, wherein the at least one amphoteric copolymer is either dissolved or dispersed in the carrier.

28. The composition according to claim 21, further comprising at least one water-insoluble carboxylic acid ester.

29. The composition according to claim 21, further comprising at least one antidandruff agent.

30. The composition according to claim 21, further comprising at least one silicone.

31. The composition according to claim 30, wherein the at least one silicone is insoluble in water.

32. The composition according to claim 21, further comprising at least one polymer selected from fixing polymers and conditioning polymers.

33. The composition according to claim 21, further comprising at least one conditioning agent selected from synthetic oils, vegetable oils, vegetable waxes, and ceramide compounds.

34. The composition according to claim 21, further comprising at least one conventional cosmetic additive selected from fatty substances; animal, fossil, mineral, and synthetic waxes; organic solvents in addition to said cosmetically acceptable carrier; thickening agents; softeners; antifoaming agents; moisturizing agents; humectants; treatment agents; antiperspirants; alkalinizing agents; acidifying agents; UV-A, UV-B, and broad-band sunscreening agents; colorants; pigments; oxidizing agents; reducing agents; perfumes; plasticizers; preservatives; anionic, cationic, nonionic, and amphoteric organic polymers in addition to said at least one amphoteric polymer; and propellants.

35. The composition according to claim 34, wherein the fatty substances are selected from mineral and animal oils.

36. A cosmetic and/or dermatological composition comprising in a cosmetically acceptable carrier, at least one amphoteric copolymer that is crosslinked and/or branched, copolymerized from a mixture, which comprises:

1) at least one monomer selected from the monomers of formulae (Ia) and (Ib):

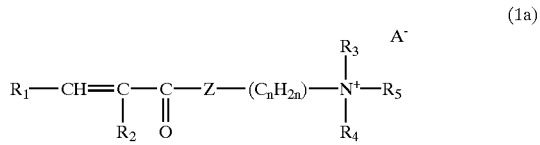

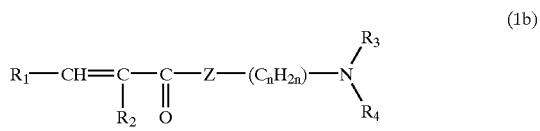

wherein $R_1$ and $R_2$, which are identical or different, are each selected from a hydrogen atom and a methyl radical; $R_3$, $R_4$, and $R_5$, which are identical or different, are each selected from linear and branched alkyl radicals having from 1 to 30 carbon atoms; Z is selected from an NH group and an oxygen atom; n is an integer ranging from 2 to 5; and $A^-$ is an anion selected from anions derived from organic and inorganic acids;

2) from 25 mol % to 75 mol % of at least one monomer of formula (II)

wherein $R_6$ and $R_7$, which are identical or different, are each selected from a hydrogen atom and a methyl radical; and $Z_1$ is selected from an OH group and a $NHC(CH_3)_2CH_2SO_3H$ group;

3) at least one monomer of formula (III):

wherein $R_6$ and $R_7$, which are identical or different, are each selected from a hydrogen atom and a methyl radical; X is selected from an oxygen atom and a nitrogen atom; and $R_8$ is selected from linear and branched alkyl radicals having from 1 to 30 carbon atoms; and 4) at least one agent selected from crosslinking and branching agents; wherein at least one of the monomers of formulae (Ia), (Ib), and (III) comprises at least one fatty chain having from 8 to 30 carbon atoms; wherein said monomers of formulae (Ia), (Ib), (II), and (III) may be quaternized; and wherein the composition is a hair styling product selected from products for washing, care, conditioning, retention of the hair style, shaping, dyeing, bleaching, permanent waving, and straightening of the hair.

37. A leave-in hair styling product, which comprises at least one amphoteric copolymer that is crosslinked and/or branched, copolymerized from a mixture, which comprises:

1) at least one monomer selected from the monomers of formulae (Ia) and (Ib):

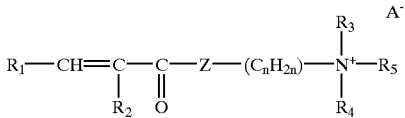

(1a)

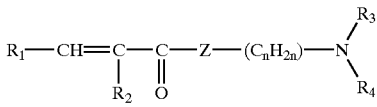

(1b)

wherein $R_1$ and $R_2$, which are identical or different, are each selected from a hydrogen atom and a methyl radical; $R_3$, $R_4$, and $R_5$, which are identical or different, are each selected from linear and branched alkyl radicals having from 1 to 30 carbon atoms; Z is selected from an NH group and an oxygen atom; n is an integer ranging from 2 to 5; and $A^-$ is an anion selected from anions derived from organic and inorganic acids;

2) from 25 mol % to 75 mol % of at least one monomer of formula (II):

(II)

wherein $R_6$ and $R_7$, which are identical or different, are each selected from a hydrogen atom and a methyl radical; and $Z_1$ is selected from an OH group and a $NHC(CH_3)_2CH_2SO_3H$ group;

3) at least one monomer of formula (III):

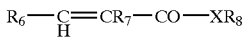

(III)

wherein $R_6$ and $R_7$, which are identical or different, are each selected from a hydrogen atom and a methyl radical; X is selected from an oxygen atom and a nitrogen atom; and $R_8$ is selected from linear and branched alkyl radicals having from 1 to 30 carbon atoms; and 4) at least one agent selected from crosslinking and branching agents;
wherein at least one of the monomers of formulae (Ia), (Ib), and (III) comprises at least one fatty chain having from 8 to 30 carbon atoms; and wherein said monomers of formulae (Ia), (Ib), (II), and (III) may be quaternized.

38. A rinse-off hair styling product, which comprises at least one amphoteric copolymer that is crosslinked and/or branched, copolymerized from a mixture, which comprises:

1) at least one monomer selected from the monomers of formulae (Ia) and (Ib):

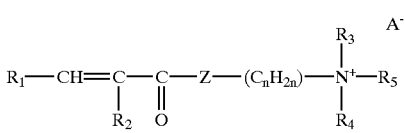

(1a)

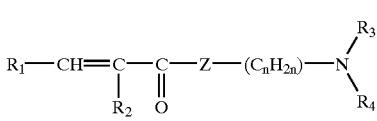

(1b)

wherein $R_1$ and $R_2$, which are identical or different, are each selected from a hydrogen atom and a methyl radical; $R_3$, $R_4$, and $R_5$, which are identical or different, are each selected from linear and branched alkyl radicals having from 1 to 30 carbon atoms; Z is selected from an NH group and an oxygen atom; n is an integer ranging from 2 to 5; and $A^-$ is an anion selected from anions derived from organic and inorganic acids;

2) from 25 mol % to 75 mol % of at least one monomer of formula (II):

(II)

wherein $R_6$ and $R_7$, which are identical or different, are each selected from a hydrogen atom and a methyl radical; and $Z_1$ is selected from an OH group and a $NHC(CH_3)_2CH_2SO_3H$ group;

3) at least one monomer of formula (III):

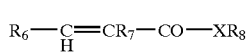

(III)

wherein $R_6$ and $R_7$, which are identical or different, are each selected from a hydrogen atom and a methyl radical; X is selected from an oxygen atom and a nitrogen atom; and $R_8$ is selected from linear and branched alkyl radicals having from 1 to 30 carbon atoms; and 4) at least one agent selected from crosslinking and branching agents; wherein at least one of the monomers of formulae (Ia), (Ib), and (III) comprises at least one fatty chain having from 8 to 30 carbon atoms; and wherein said monomers of formulae (Ia), (Ib), (II), and (III) may be quaternized.

39. The composition according to claim 36, wherein the hair styling product is selected from shampoos and hair conditioners.

40. The composition according to claim 38, wherein the rinse-off hair styling product is selected from shampoos and hair conditioners.

41. The composition according to claim 21, wherein the composition is a rinse-off care and/or hygiene product.

42. The composition according to claim 21, wherein the composition is a make-up remover.

43. The composition according to claim 21, wherein the composition is a make-up product.

44. The composition according to claim 43, wherein the make-up product is selected from nail varnishes and care bases for the nails.

45. The process according to claim 1, wherein said at least one amphoteric copolymer is a conditioning agent or an additive for a conditioning agent.

46. The composition according to claim 21, wherein said at least one amphoteric copolymer is a conditioning agent or an additive for a conditioning agent.

47. A method of treating a keratinous material comprising applying to said keratinous material a cosmetic and/or dermatological composition comprising in a cosmetically acceptable carrier, at least one amphoteric copolymer that is crosslinked and/or branched, copolymerized from a mixture, which comprises:

1) at least one monomer selected from the monomers of formulae (Ia) and (Ib):

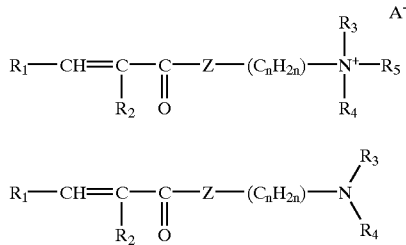

(1a)

(1b)

wherein $R_1$ and $R_2$, which are identical or different, are each selected from a hydrogen atom and a methyl radical; $R_3$, $R_4$, and $R_5$, which are identical or different, are each selected from linear and branched alkyl radicals having from 1 to 30 carbon atoms; Z is selected from an NH group and an oxygen atom; n is an integer ranging from 2 to 5; and $A_-$ is an anion selected from anions derived from organic and inorganic acids;

2) from 25 mol % to 75 mol % of at least one monomer of formula (II):

(II)

wherein $R_6$ and $R_7$, which are identical or different, are each selected from a hydrogen atom and a methyl radical; and $Z_1$ is selected from an OH group and a $NHC(CH_3)_2CH_2SO_3H$ group;

3) at least one monomer of formula (III):

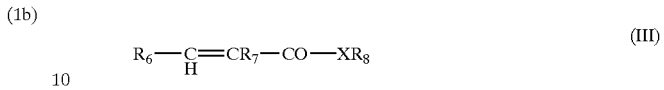

(III)

wherein $R_6$ and $R_7$, which are identical or different, are each selected from a hydrogen atom and a methyl radical; X is selected from an oxygen atom and a nitrogen atom; and $R_8$ is selected from linear and branched alkyl radicals having from 1 to 30 carbon atoms; and 4) at least one agent selected from crosslinking and branching agents;

wherein at least one of the monomers of formulae (Ia), (Ib), and (III) comprises at least one fatty chain having from 8 to 30 carbon atoms; and wherein said monomers of formulae (Ia), (Ib), (II), and (III) may be quaternized.

* * * * *

UNITED STATES PATENT AND TRADEMARK OFFICE
CERTIFICATE OF CORRECTION

PATENT NO.    : 6,589,539 B1                                       Page 1 of 1
DATED         : July 8, 2003
INVENTOR(S)   : Henri Sebag et al.

It is certified that error appears in the above-identified patent and that said Letters Patent is hereby corrected as shown below:

<u>Column 7,</u>
Line 15, "(I), and (III)" should read -- (II), and (III) --; and
Line 33, delete space between "methyl" and "propanesulphonic --.

Signed and Sealed this

Fourteenth Day of October, 2003

JAMES E. ROGAN
*Director of the United States Patent and Trademark Office*